United States Patent
Hagelganz et al.

(10) Patent No.: US 9,089,386 B2
(45) Date of Patent: Jul. 28, 2015

(54) SELF-LIGATING BRACKET WITH SLIDING COVER

(71) Applicant: World Class Technology Corporation, McMinnville, OR (US)

(72) Inventors: Rolf Hagelganz, Dundee, OR (US); Juergen Bathen, McMinnville, OR (US)

(73) Assignee: World Class Technology Corporation, McMinnville, OR (US)

( * ) Notice: Subject to any disclaimer, the term of this patent is extended or adjusted under 35 U.S.C. 154(b) by 0 days.

(21) Appl. No.: 14/079,527

(22) Filed: Nov. 13, 2013

(65) Prior Publication Data

US 2014/0141383 A1  May 22, 2014

Related U.S. Application Data

(63) Continuation-in-part of application No. 13/679,019, filed on Nov. 16, 2012.

(60) Provisional application No. 61/779,630, filed on Mar. 13, 2013.

(51) Int. Cl.
*A61C 7/30* (2006.01)
*A61C 7/28* (2006.01)

(52) U.S. Cl.
CPC .. *A61C 7/287* (2013.01); *A61C 7/30* (2013.01)

(58) Field of Classification Search
CPC .............. A61C 7/00; A61C 7/12; A61C 7/14; A61C 7/141; A61C 7/143; A61C 7/145; A61C 7/148; A61C 7/16; A61C 7/22; A61C 7/28; A61C 7/287; A61C 7/30; A61C 7/34

USPC ................................... 433/2, 8–11, 13, 16, 18
See application file for complete search history.

(56) References Cited

U.S. PATENT DOCUMENTS

| | | | |
|---|---|---|---|
| 5,275,557 A | 1/1994 | Damon | |
| 5,322,435 A * | 6/1994 | Pletcher | 433/11 |
| 5,429,500 A | 7/1995 | Damon | |
| 5,439,378 A * | 8/1995 | Damon | 433/8 |
| 5,466,151 A | 11/1995 | Damon | |
| 5,618,176 A | 4/1997 | Andreiko et al. | |
| 6,071,118 A * | 6/2000 | Damon | 433/9 |
| 6,257,883 B1 * | 7/2001 | Voudouris | 433/11 |
| 7,267,545 B2 | 9/2007 | Oda | |
| 7,416,408 B2 | 8/2008 | Farzin-Nia et al. | |
| 7,419,375 B2 | 9/2008 | Farzin-Nia et al. | |
| 7,621,743 B2 | 11/2009 | Bathen et al. | |
| 7,674,110 B2 | 3/2010 | Oda | |
| 7,704,072 B2 | 4/2010 | Damon | |
| 7,785,101 B2 * | 8/2010 | Forster | 433/11 |
| 7,909,603 B2 | 3/2011 | Oda | |

(Continued)

*Primary Examiner* — Cris L Rodriguez
*Assistant Examiner* — Justin O'Donnell
(74) *Attorney, Agent, or Firm* — Chernoff, Vilhauer, McClung & Stenzel LLP (57) ABSTRACT

A self-ligating orthodontic bracket has a sliding archwire cover that has a top surface congruent with the top surface of an upper body portion having an archwire slot. The cover has a resilient locking tab that slides across the slot, bending upward as it encounters a ridge on the other side of the slot, and latching to the ridge to secure the cover in a closed position. The cover has a modified dovetail shape with flared bottom portions that slideably engage guides for reciprocal opening and closing sliding motion. A groove in the slide support track engages the locking tab in the open position preventing it from disengaging from the upper body portion.

5 Claims, 11 Drawing Sheets

(56) References Cited

U.S. PATENT DOCUMENTS

| | | |
|---|---|---|
| 7,963,767 B2 * | 6/2011 | Lewis et al. ............... 433/10 |
| 8,029,276 B1 | 10/2011 | Lokar |
| 8,033,824 B2 | 10/2011 | Oda et al. |
| 8,113,827 B2 | 2/2012 | Farzin-Nia et al. |
| 8,246,347 B2 | 8/2012 | Oda |
| 8,251,696 B2 | 8/2012 | Rodriguez et al. |
| 8,414,292 B2 | 4/2013 | Lopes |
| 8,469,704 B2 | 6/2013 | Oda et al. |
| 2002/0119414 A1 * | 8/2002 | Orikasa ............... 433/10 |
| 2002/0132206 A1 | 9/2002 | Voudouris |
| 2009/0325120 A1 | 12/2009 | Lewis et al. |
| 2010/0178629 A1 * | 7/2010 | Oda et al. ............... 433/14 |

* cited by examiner

SELF-LIGATING BRACKET WITH SLIDING COVER

CROSS-REFERENCE TO RELATED APPLICATIONS

This application is a continuation-in-part application of pending U.S. patent application Ser. No. 13/679,019 filed Nov. 16, 2012. This application also claims priority based upon U.S. provisional application Ser. No. 61/779,630 filed Mar. 13, 2013.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

1. Field of the Invention

This disclosure relates to improved self-locking or ligatureless orthodontic brackets.

2. Description of Related Art Including Information Disclosed Under 37 CFR 1.97 and 1.98.

Several self-locking or self-ligating (ligatureless) orthodontic brackets have been designed. However, most of those have complex designs, incorporating features requiring prohibitively expensive machining operations or comprising multiple separate parts, which in turn increases the number of failure modes for such brackets. Other designs have been rejected in the marketplace due to poor quality or poor design, a lack of available features, difficulty of use, or other factors.

One such bracket is disclosed in U.S. Pat. No. 7,621,743 entitled Orthodontic Bracket. That device is a self-ligating bracket that includes a locking slide cover that entrains an archwire. However, like many sliding covers, the top surface is not smooth, which is important for patient comfort. Moreover, this device is difficult to manufacturer requiring small interlocking extensions mating in the plane of the slide and guide members on either side having sharp edges that protrude outwardly which have a tendency to irritate the mouth of the user.

Another construction is shown in U.S. Pat. No. 8,414,292. In this patent, a keyhole-shaped clip slides across an archwire slot and two wings on the clip engage stops to lock the clip in place. The locking clip is tiny, and because it is flat, it is rather flimsy and prone to failure.

BRIEF SUMMARY OF THE INVENTION

A self-ligating orthodontic bracket has an archwire cover that slides in a guide channel across an archwire slot. A flexible locking tab at the cover's leading edge engages a ridge on the other side of the archwire slot. It flexes up and over a ridge and a spring restoring force locks it in place once it has cleared the ridge.

The foregoing and other objectives, features, and advantages of the invention will be more readily understood upon consideration of the following detailed description of the invention taken in conjunction with the accompanying drawings.

DETAILED DESCRIPTION OF PREFERRED EMBODIMENTS

Orthodontic treatment generally comprises dental work to correct irregularities of the teeth or of the relation of the teeth to surrounding anatomy. The irregularities may involve malocclusions with varying degrees of severity. Class 1 malocclusions, for example, may involve spacing irregularities such as excessive crowding or diastema (a gap between two adjacent teeth). Class 2 malocclusions may involve overbite conditions where the upper anterior teeth project labially over the lower anterior teeth. Class 3 malocclusions, in contrast, may involve underbite conditions where the upper anterior teeth close within the lingual side of the lower anterior teeth. For these and other observed irregularities, treatment typically involves installation of braces or mechanical aids for repositioning the teeth into correct orthodontic alignment.

Braces generally include orthodontic brackets configured for attachment to the labial or lingual surfaces of the teeth or for attachment to metallic bands secured around the teeth. The brackets typically include archwire slots within which a flexible yet resilient archwire may be engaged. Typically, each bracket is bonded to the tooth surface so that the bracket's archwire slot is oriented for engagement with the archwire. Various techniques are used for orienting the brackets. For example, an edgewise appliance comprises braces whereby each bracket is oriented and bonded to the tooth so that the archwire slot is perpendicular to the long axis of the root of the tooth. Alternatively, a straight-wire appliance includes braces whereby each bracket is oriented and bonded to the tooth so that the archwire slot is parallel to the occlusal plane (the biting surfaces of the teeth).

The archwire is typically a curved metallic wire having a rectangular or circular cross section that is bent or twisted prior to engagement with the brackets. The memory or restoring force exerted by the archwire upon the brackets serves to move the teeth into the desired alignment. Throughout the duration of orthodontic treatment, the orthodontist periodically adjusts the shape of the archwire (as well as the configuration of other attachments such as elastic bands and so forth) to achieve the correct orthodontic alignment.

Most brackets in current use incorporate tie wings or extensions that project upwardly and downwardly in a gingival-occlusal orientation and require the use of ligatures or ligating modules to hold the archwire within the archwire slots. The ligatures or ligating modules are typically donut-shaped elastomeric rings or wires that are stretched around or twisted around the tie wings.

The use of such ligatures or ligating modules presents a number of inherent disadvantages, some of which are mentioned herein. The small size of the ligatures or ligating modules requires substantial time for installation of the archwire. Because the orthodontist will typically make numerous adjustments to the archwire throughout orthodontic treatment, the orthodontist will likely remove and replace the ligatures or ligating modules numerous times. Hygiene is another problem since the use of ligatures or ligating modules increases the areas where food particles may be trapped. Further, with movement due to chewing or other activities, the ligatures or ligating modules may become detached altogether, allowing the archwire to disengage from the archwire slots.

Ligatures or ligating modules also present other limitations in terms of the forces exerted upon the brackets. For example, the labial or outward force that may be applied to a tooth having a bracket bonded to its labial surface is limited to the strength of the ligature or ligating module in the labial direction. On the same tooth, the force that may be applied in the lingual direction is not so constrained (because the force is applied against the bracket structure rather than the ligature or ligation module). Similarly, the longitudinal (or mesial-distal) forces, which may be applied along the direction of the archwire, may be limited or defined by the friction between the ligature or ligation module and the archwire. By contrast, a means for locking the archwire within the archwire slot would enhance the forces that may be exerted along the direction of the archwire. Likewise, a means for slideably retaining the archwire within the archwire slot would allow greater flexibility than available from brackets requiring the use of ligatures or ligation modules.

Figure 1:
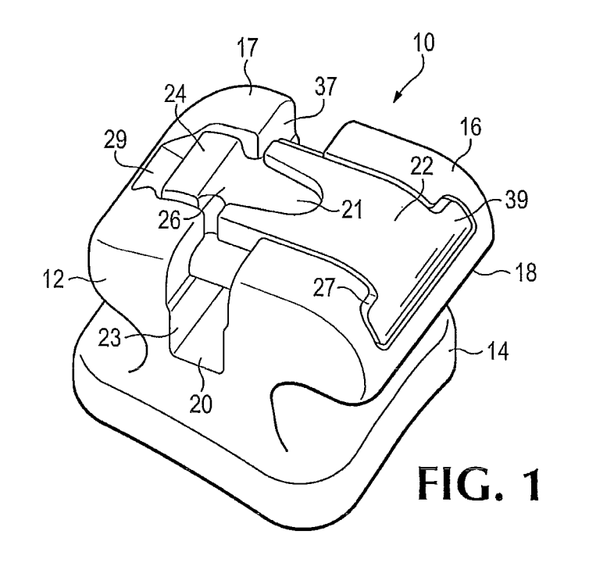
FIG. 1 is a perspective view of a self-ligating orthodontic bracket with a sliding archwire slot cover in a closed position.
Figure 2:
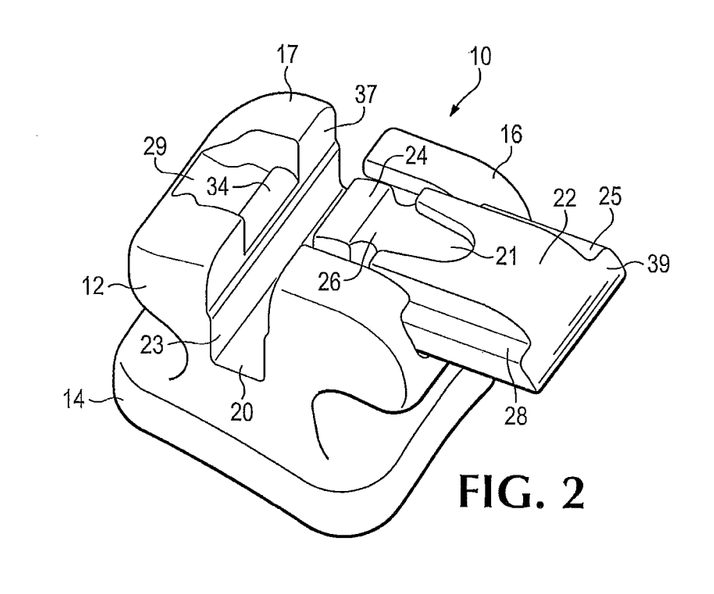
FIG. 2 is a perspective view of the orthodontic bracket of FIG. 1 with the sliding cover in the open position.

A self-ligating orthodontic bracket 10 includes two separate parts, which together comprise a bracket assembly. A bracket body 12 includes a base portion 14 that is secured to a patient's tooth (not shown) with an adhesive or the like. The base portion 14 supports an upper body 16 that includes a pair of tie wing portions 17, 18, one portion extending in the gingival direction and the other portion oriented in the occlusal direction. It is to be understood that these directions may be reversed depending upon the bracket's position and the preference of the designer. The upper body 16 has an archwire slot 20 that extends in a mesial-distal direction when the bracket 10 is installed on a patient's tooth. The archwire slot 20 has a first sidewall 19 and a second sidewall 23. The second part is a sliding cover 22 that engages the upper body 16 and is selectively opened and closed over the archwire slot 20 so as to retain the archwire (not shown) or to provide access to the archwire slot 20 for installation, removal, and/or adjustment.

The sliding cover 22 has a lower portion 24 that resembles a semi-dovetail shape. Rounded lower side portions 25, 28 flare outwardly beyond the width of the top surface portion. These side portions engage a guide channel 27 in the upper tie wing portion 18 of the bracket 20. The guide channel 27 overlaps the side portions of the cover 25, 28 and retains the cover 22 as it slides forward. A depression 21 in the top surface of the cover permits an orthodontist to use a tool to manipulate the sliding cover from a locked to an unlocked position. On the opposite side of the archwire slot is a receiving space 29 into which a locking tab nests when the slide cover is in a fully closed position.

The sliding cover 22 has a flexible locking tab 24 on its forward end. The locking tab is joined to the main body of the sliding cover by a narrow neck 26 of reduced height and width. The neck 26 provides elasticity so that the locking tab 24 can flex in an upward (labial) direction relative to the base 14 and spring back into a locked position under the restoring force of the flexible neck 26. No particular shape is necessary for providing enough flex for the locking tab 24, and other shapes such as a relief channel or merely making the tab out of a material that permits it to act like a leaf spring are also contemplated. The locking tab 24 has a rounded leading edge 30 in front and a straight undercut surface 32 behind the leading edge so that the front part of the locking tab 24 forms a hook.

Figures 3, 4, 5:
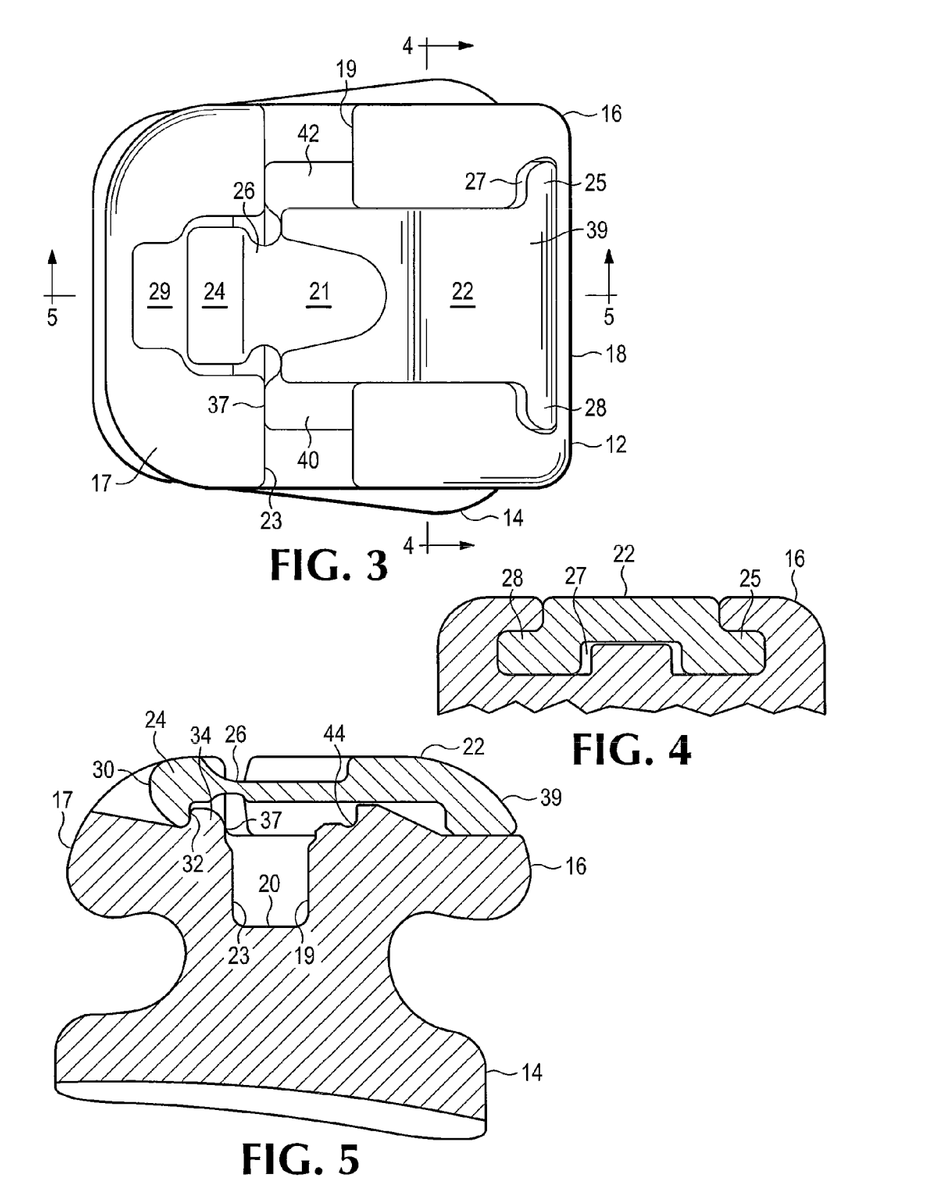
FIG. 3 is a top view of the orthodontic bracket of FIG. 1.
FIG. 4 is a sectional view taken along line 4-4 of FIG. 3.
FIG. 5 is a sectional view taken along line 5-5 of FIG. 3.
Figure 6:
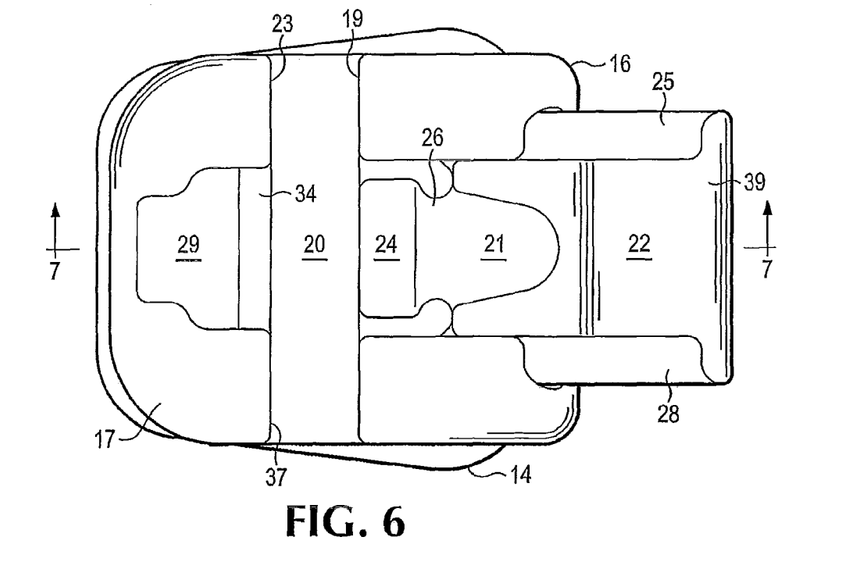
FIG. 6 is a top view of the orthodontic bracket of FIG. 2.

The leading edge of the tab 24 slides across a ridge 34 as the cover 22 is urged across the archwire slot 20. The front surface of the ridge 34 is curved or angled so that the rounded leading edge 30 easily slides up and over it. This forces the tab 24 to flex upwardly. Once the leading edge 30 clears the ridge 34, it snaps down onto the back of the ridge effectively latching the cover 22 in a closed position. The sliding cover 22 has a length dimension such that when the cover is closed, the forward ends 40, 42 of the flared side portions 25, 28 abut a wall 37 of the tie wing portion 17, and the back end 39 of the sliding cover 22 is flush with the upper body 16 forming essentially a smooth and continuous surface. Thus, there are no sharp protruding parts to irritate the patient's mouth.

To open the archwire slot 20, a tool (not shown) is inserted into the depression 21 in the top of the cover 22 and the cover is pulled back. The locking tab 24 flexes upward as the cover 22 retracts, clearing the ridge 34. The neck 26 is formed so that the spring action of the tab is not too stiff to resist the ramping action of the tab 24 over the ridge 34 as the cover is retracted.

Figure 7:
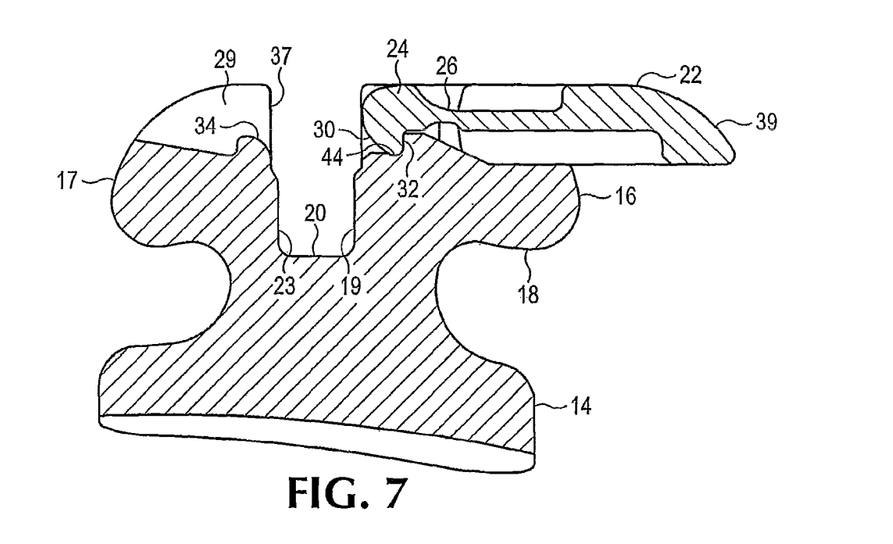
FIG. 7 is a sectional view taken along line 7-7 of FIG. 6.

In its retracted position, the locking tab 24 rests in a groove 44 on the opposite side of the archwire slot. This prevents the sliding cover from becoming separated from the body of the bracket. It also defines the amount of travel of the sliding cover from open position to closed position.

Figure 8:
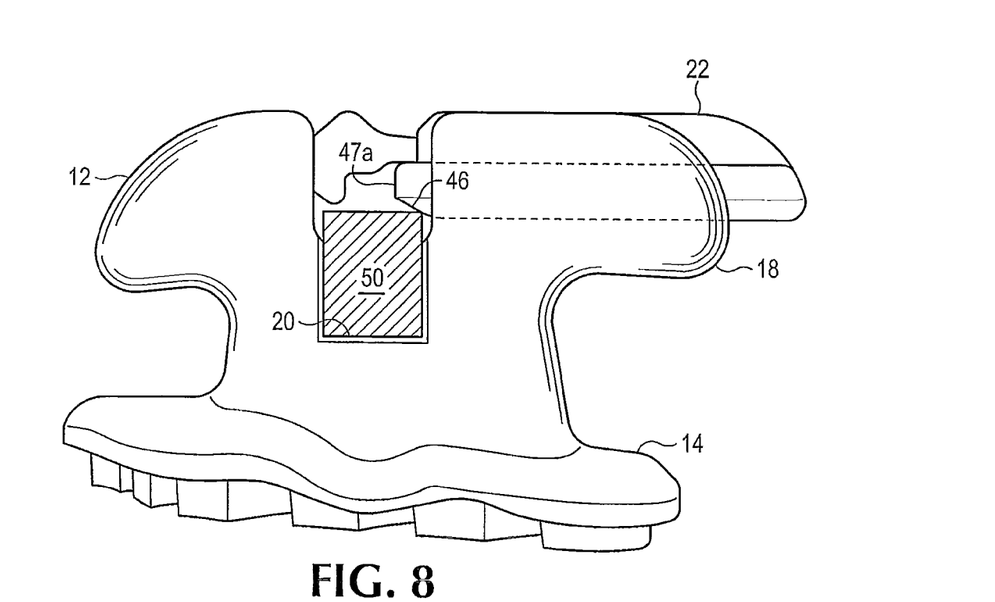
FIG. 8 is a side elevation view of another embodiment of a self-ligating orthodontic bracket in an open position.
Figure 8A:
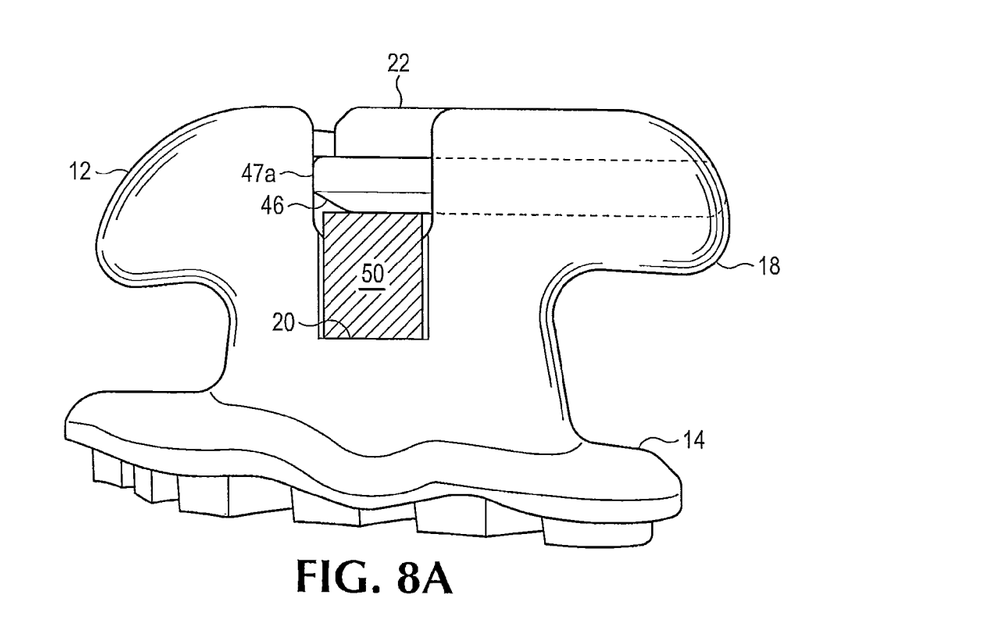
FIG. 8A is a side elevation view of the bracket of FIG. 8 in the closed position.

FIGS. 8 and 8A show an alternate version of the sliding cover of FIGS. 1-7. The lingual front edges 47a and 47b of the two side portions 26, 28 of the cover 22 each have a chamfered edge 46. With a chamfered edge as an underside surface, the cover more easily engages the archwire 50 and acts like a sliding inclined plane, pushing the archwire 50 into the slot 20 so that it contacts the bottom surface of the slot. This makes for better coupling of torqueing forces to be transferred to the teeth.

Figure 9:
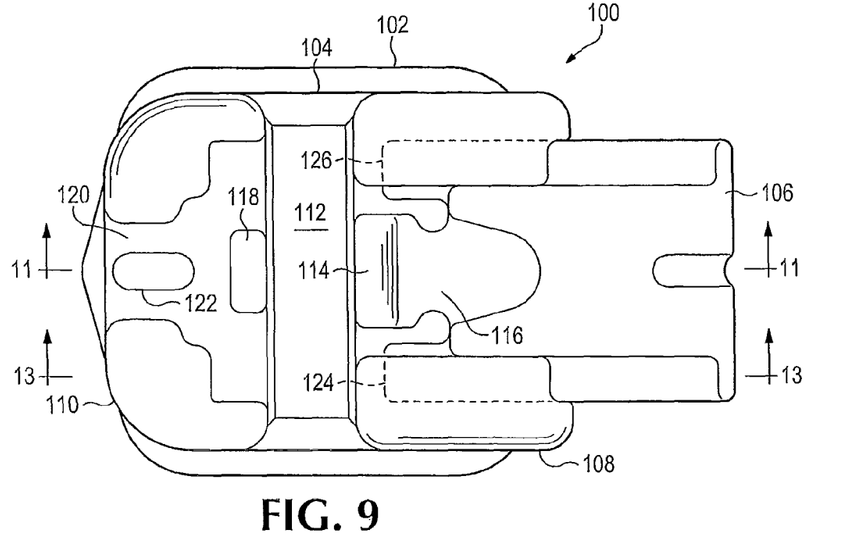
FIG. 9 is a top view of an alternate embodiment of an orthodontic bracket in the open position.
Figure 10:
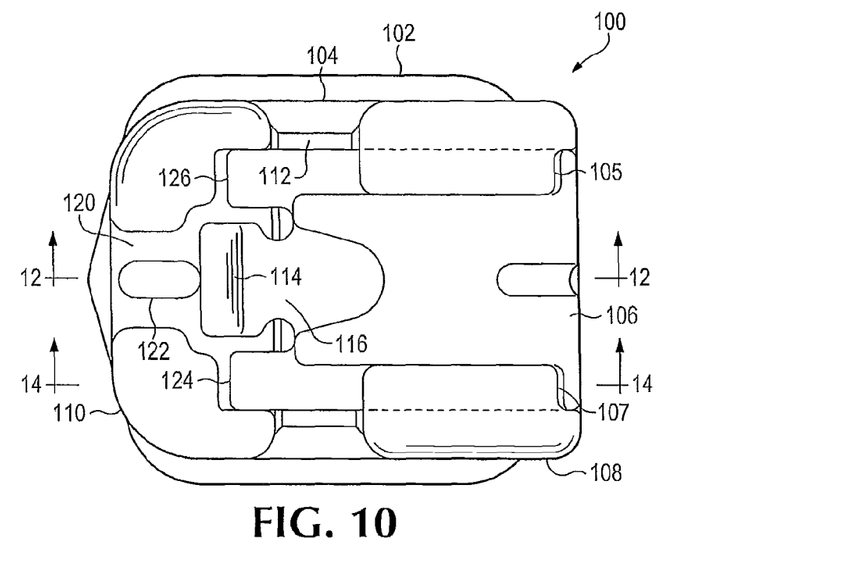
FIG. 10 is a top view of the bracket of FIG. 9 in the closed position.

An alternate bracket construction is shown in FIG. 9. Bracket 100 has a base 102 and a body portion 104. The base 102 and body 104 are a single piece, preferably formed through the process of metal injection molding. A single piece molded bracket is much stronger than a conventional two piece unit in which the base and the upper body are formed separately then attached to each other. A sliding archwire slot cover 106 provides self ligation. The body portion 104 comprises two parts, a gingival portion 108 housing the cover 106 and an occlusal portion 110 which receives the cover when it closes. Labeling these parts as gingival and occlusal portions is for convenience in description only, and in actual practice the orientation of the bracket could be reversed, if desired.

Figure 11:
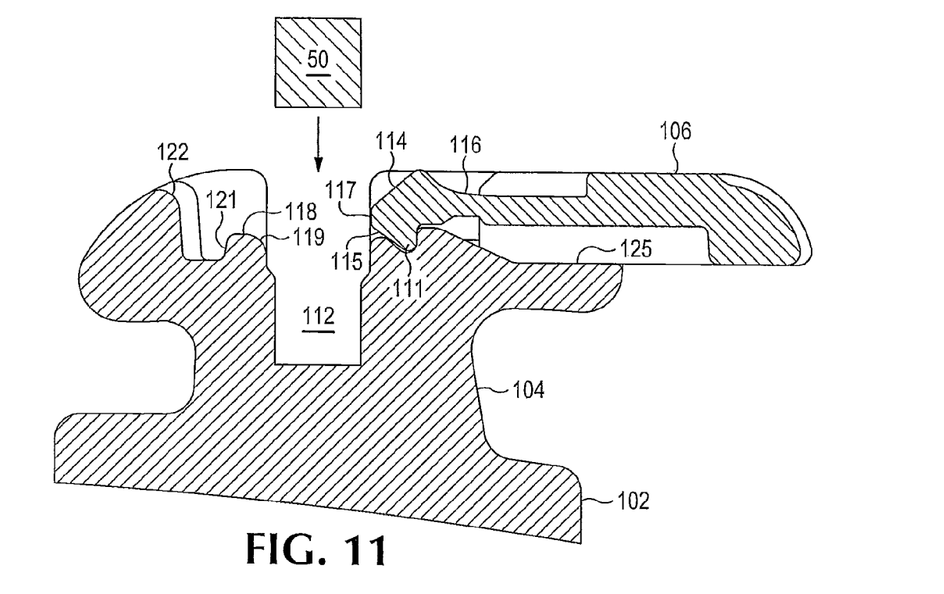
FIG. 11 is a side cutaway view taken along line 11-11 in FIG. 9.
Figure 12:
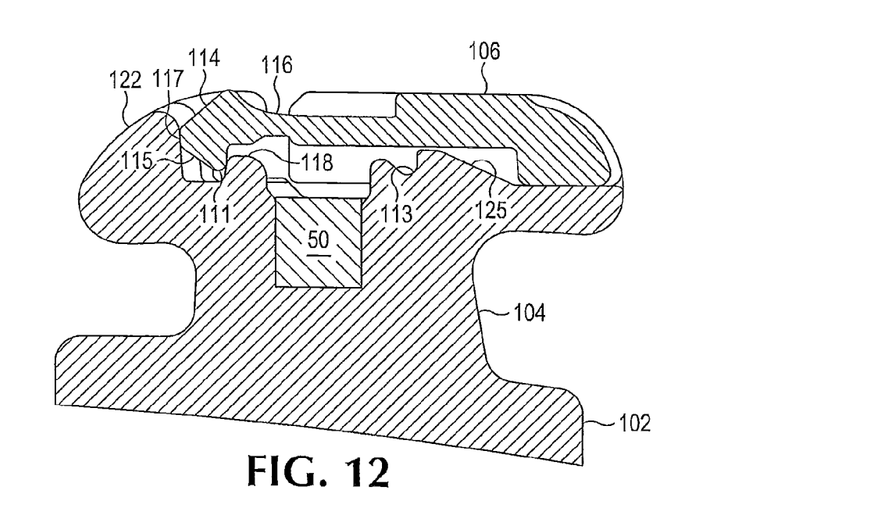
FIG. 12 is a side cutaway view taken along line 12-12 in FIG. 10.
Figure 13:
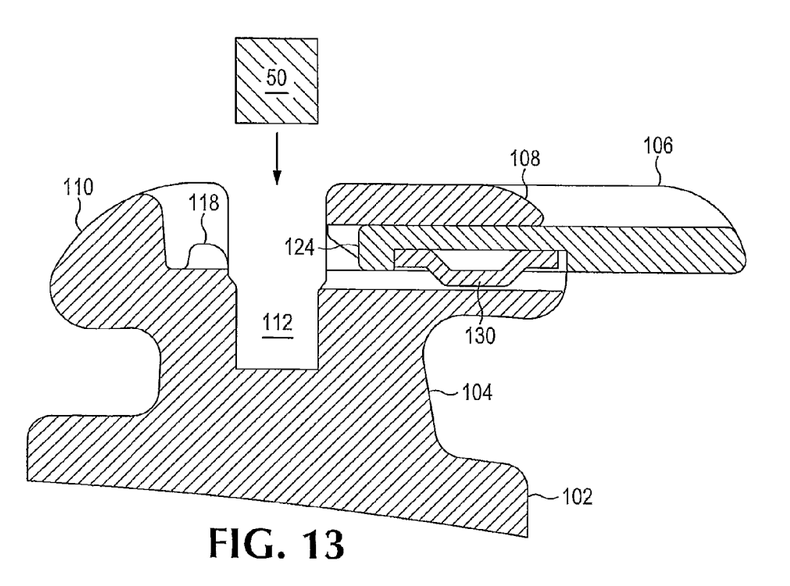
FIG. 13 is a side cutaway view taken along line 13-13 in FIG. 9.
Figure 14:
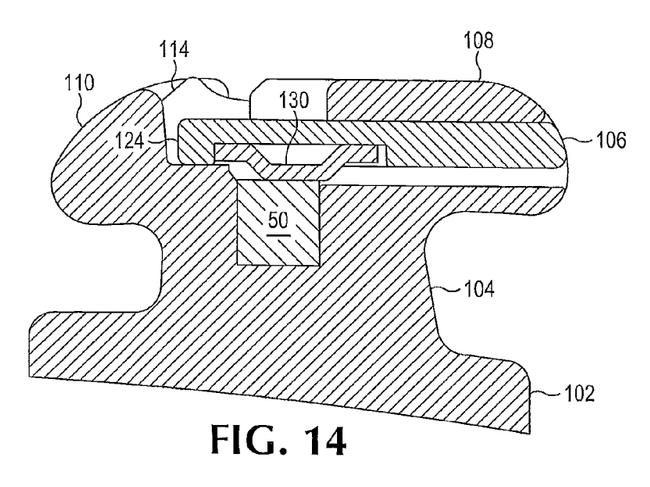
FIG. 14 is a cutaway view taken along line 14-14 in FIG. 10.
Figure 15:
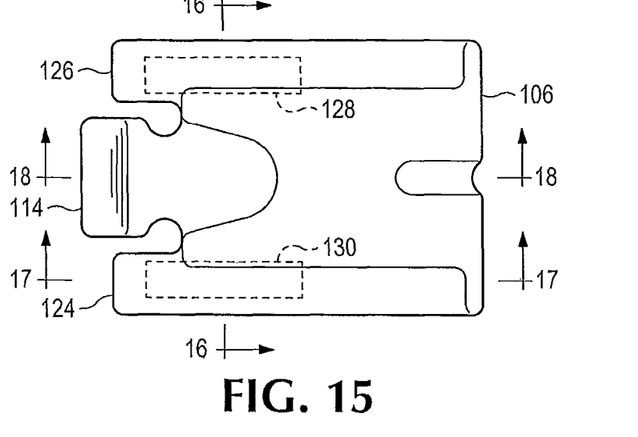
FIG. 15 is a top view of an alternate construction of a sliding archwire cover used in the embodiment of FIG. 9.
Figure 16:
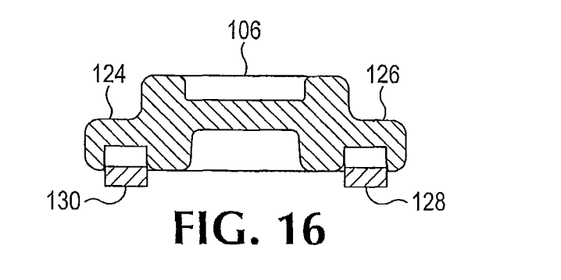
FIG. 16 is a cutaway view taken along line 16-16 in FIG. 15.
Figure 17:
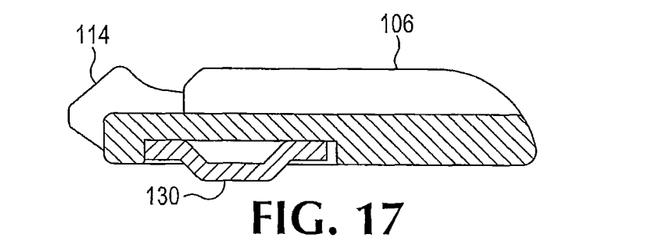
FIG. 17 is a cutaway view taken along line 17-17 in FIG. 15.
Figure 18:
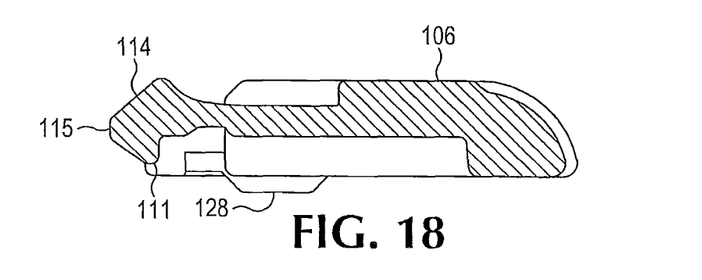
FIG. 18 is a side cutaway view taken along line 18-18 in FIG. 15.

In the embodiment of FIGS. 9-12, the cover 106 includes a pair of side wing portions 126 and 124. These portions fit within guide channels 105, 107 similar to those shown in FIG. 4 and slide all the way across the archwire slot 112 to a ledge 120 on the gingival side of the upper bracket body, thus firmly locking the archwire in the slot The sliding cover 106 is similar to the cover of FIG. 1. A flexible locking tab portion 114 is joined to the main body of the cover 106 by a narrow neck 116. As FIG. 11 shows, the neck 116 is thin in the lingual-labial plane as well as narrow in the mesial-distal plane. This permits the tab portion 114 to flex upward (in a labial direction) when the tab encounters a ridge 118 as the cover moves from an open to a closed position. The nose 117 of the locking tab 114 has an inclined planar surface 115 that engages a curved portion 119 of the ridge 118 that is adjacent the archwire slot as the sliding cover 106 is moved from an open toward a closed position. The inclined planar surface 115 meets the curved ridge surface 119, and as the cover 106 slides over the slot, the locking tab 114 flexes in a labial direction until it clears the ridge 118. Once this occurs, the tab portion 114, under the restoring force action of the thin neck 116, which acts as a spring, snaps down, and locks onto the ridge. A hook portion 111 of the locking tab 114 effectively latches the sliding cover shut by engaging the back surface 121 of the ridge 118. At the same time the nose 117 of the tab portion 114 contacts a stop 122 thus preventing further forward movement. The interaction of the inclined plane 115 with the curved ridge surface 119 under the force of the forward movement of the sliding cover efficiently latches the sliding cover without requiring an undue amount of force to move the locking tab up and over the ridge. It will be understood that the front of the ridge may assume other shapes that could work equally well such as a slanted or inclined surface. Similarly the nose portion of the locking tab need not be an inclined plane, but could be merely curved. What is important is not the specific form of these surfaces, but that they are formed to slide smoothly against each other and provide some mechanical advantage to overcome the stiffness of the spring effect of the neck 116.

When the cover 106 is to be retracted to an open position the process is reversed, and the cover is slid back until the hook 111 is caught by a groove 113 in the slide track 125 of the occlusal portion 108 thus preventing any further rearward movement.

FIGS. 13-18 show an embodiment of the sliding cover that may be used as an alternative to the sliding cover of FIGS. 8 and 8A. The cover 106 is in all other respects the same as that illustrated in FIGS. 9-12, but instead of using chamfered undersurfaces on the sliding cover, it employs insertable leaf springs to push the archwire into the archwire slot. The side wing portions 126 and 124 of the sliding cover 106 have underside (lingual) pockets that are fitted with insertable leaf springs 128 and 130. When the cover 106 moves from an open to a closed position, entraining the archwire 50 in the slot 112, the leaf springs 128, 130 apply pressure to the top of the archwire and press it down into the slot.

FIGS. 19-25 illustrate another alternative embodiment of a self ligating bracket. This bracket is of single piece construction as well and may be made of a clear or translucent material such as a plastic co-polymer. A bracket 200 includes a base 202 and an upper body portion 204 with an occlusal side 206 and a gingival side 208 separated by an archwire slot 210. Preferably the bracket 200 is of single piece construction formed by a three dimensional printing process.

Figure 19:
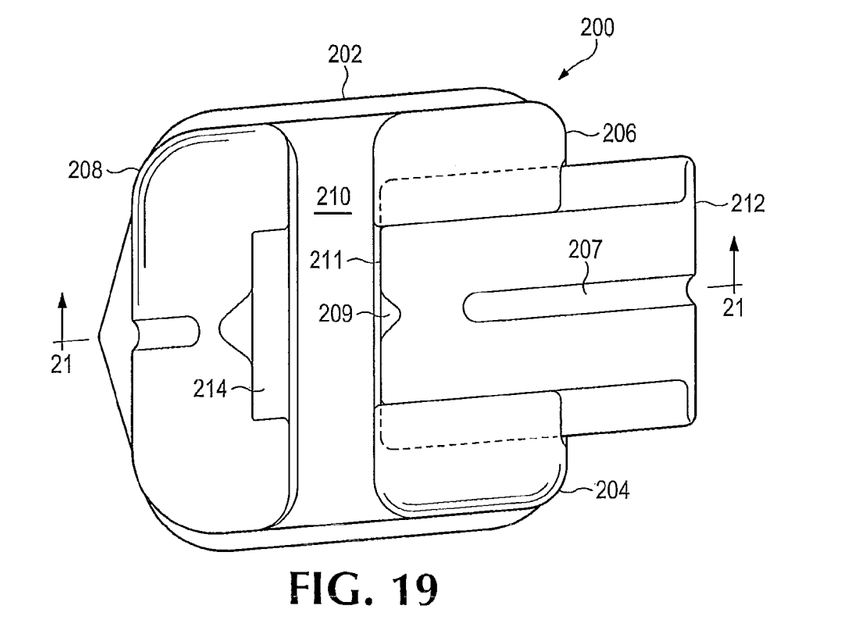
FIG. 19 is a top view of another embodiment of a self ligating bracket with a sliding cover in an open position.
Figure 20:
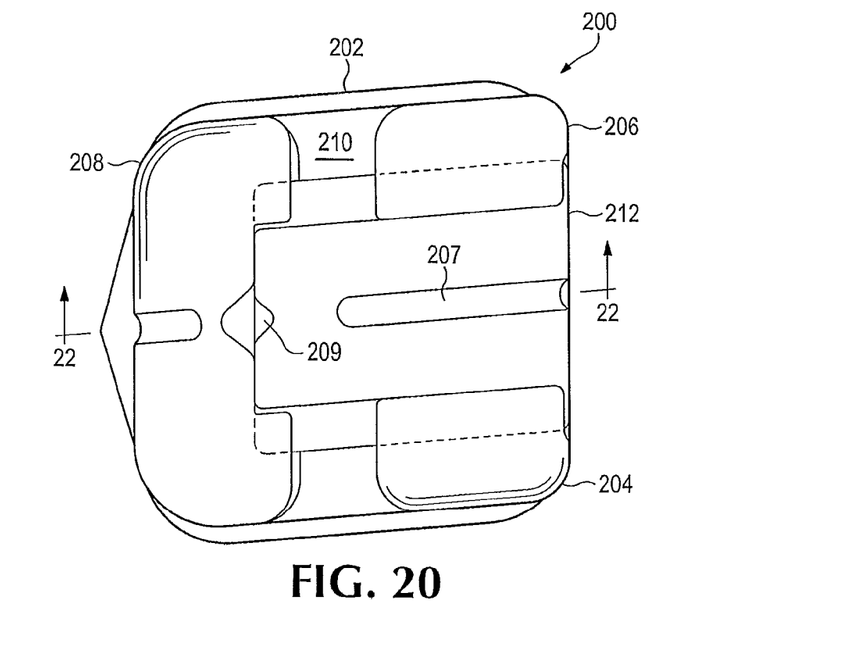
FIG. 20 is a top view of the embodiment of the self ligating bracket of FIG. 19 with the sliding cover in a closed position.
Figure 23:
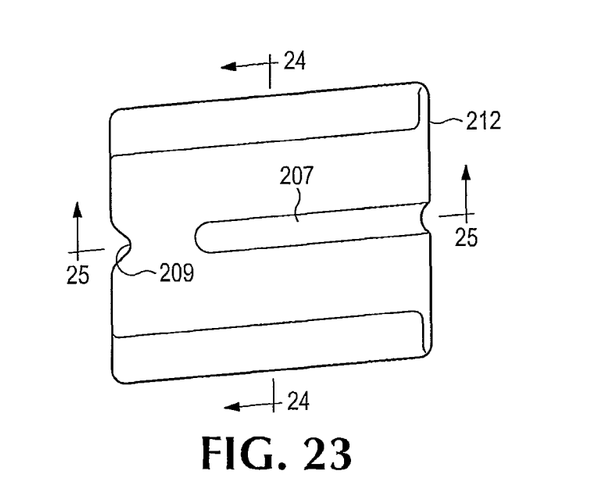
FIG. 23 is a top view of a sliding cover used in the embodiment of FIG. 19.
Figure 24:
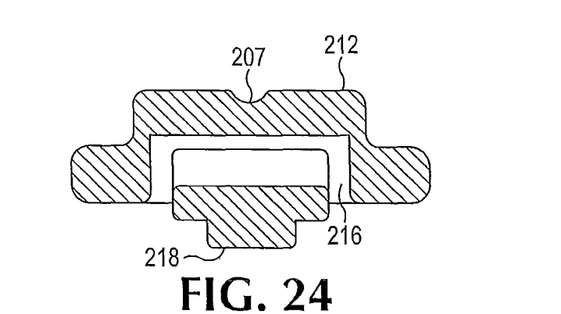
FIG. 24 is a cutaway view taken along line 24-24 in FIG. 23.
Figure 25:
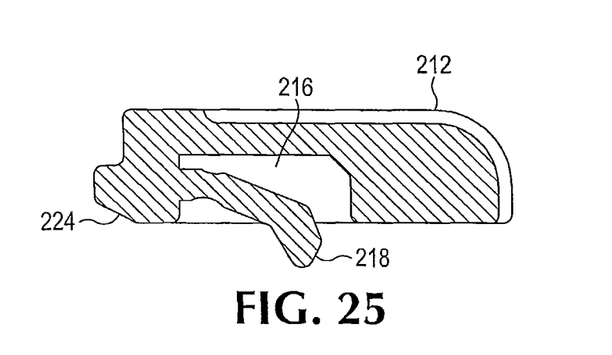
FIG. 25 is a cutaway view taken along line 25-25 in FIG. 23.

A sliding cover 212 slides across the archwire slot 210 to close over and entrain an archwire (not shown) therein. The cover 212 has a leading edge 211 that slides across the slot 210 and in the closed position engages a ledge 214 formed in the gingival side 208 of the upper body portion 204. The cover's top surface includes a small depression 209 which may be engaged by a manipulator tool (not shown) to open the cover 212. A groove 207 in the top surface provides a means for engaging the cover with the tool to slide it into a closed position.

Figure 21:
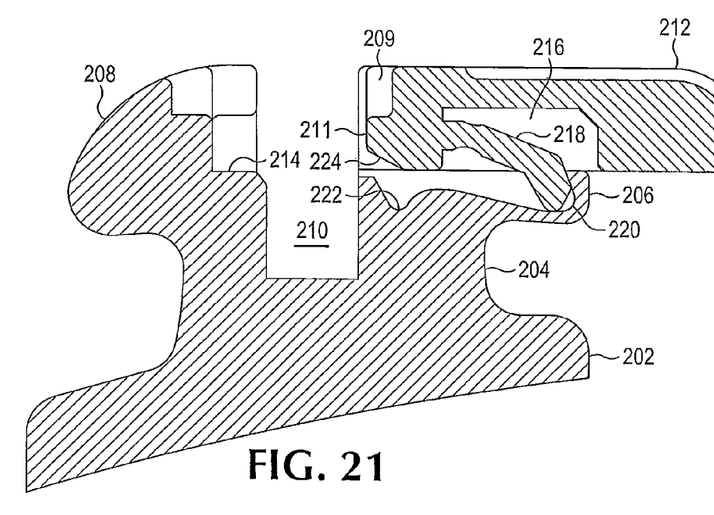
FIG. 21 is a cutaway view taken along line 21-21 in FIG. 19.
Figure 22:
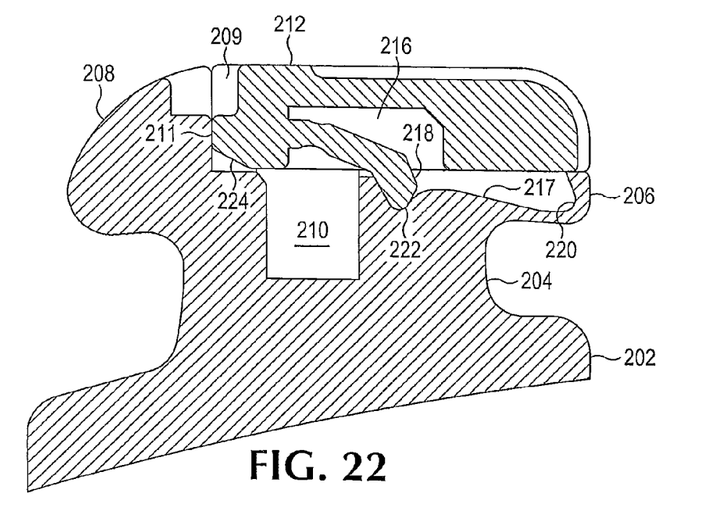
FIG. 22 is a cutaway view taken along line 22-22 in FIG. 20.

Referring to FIGS. 21 and 22, the sliding cover 212 has a recess 216 formed in its lingual underside. A downwardly (lingually) depending leaf spring 218 is adapted to flex within the recess 216 and engages a rear stop groove 220 in the occlusal side 206 of the bracket when the sliding cover is in an open position. This limits rearward movement of the sliding cover and prevents its dislodging from the upper body portion 204. When the cover is moved forward to a closed position, the spring 218 flexes upwardly within the recess as it slides over a curved surface 217 that extends between the rear stop groove 220 and a latching groove 222, and then snaps downwardly into the latching groove 222 to lock the cover in place over the archwire slot 210. As in the embodiment of FIGS. 8 and 8A, the leading edge 211 of the cover 212 may have a chamfered undersurface 224 that aids in pushing the archwire into the slot.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:
1. A self-ligating orthodontic bracket comprising:
a body having a base surface adapted to be affixed to a tooth, said body having a first upper tie wing portion and a second upper tie wing portion, said first upper tie wing portion being separated from said second upper tie wing portion by an archwire slot extending through the body in a mesial-distal direction;

said second upper tie wing portion having a ridge, said ridge having a front surface adjacent said archwire slot and a back surface;

a ligating archwire cover slidably mounted on said first upper tie wing portion, and supported by said first upper tie wing portion when said cover is in an open position exposing said archwire slot, said archwire cover having a centrally disposed, forwardly extending flexible locking tab, wherein said locking tab is adapted to flex in a labial direction when said cover is moved from said open position toward a closed position covering said archwire slot and said locking tab engages said ridge, and is adapted to flex in a lingual direction to latch said archwire cover in a closed position thereby covering said archwire slot when said locking tab moves over said ridge wherein said locking tab comprises a slanted nose portion for engaging said front surface of said ridge, and further comprises a hook portion for latching said cover to the back surface of said ridge, and wherein said first upper tie wing portion includes a groove for engaging said hook portion when said archwire cover is moved from a closed position to an open position.

2. The self-ligating orthodontic bracket of claim 1 wherein said front surface of said ridge is slanted or curved.

3. The self-ligating bracket of claim 1 wherein said archwire cover further includes a pair of side wing portions on either side of said locking tab, said pair of side wing portions each having a chamfered lingual surface adjacent leading edges thereof.

4. The self-ligating bracket of claim 1 wherein said archwire cover further includes a pair of side wing portions on either side of said locking tab, said pair of side wing portions each having an underside pocket adapted to receive an insertable, lingually flexing leaf spring for engaging an archwire when said sliding cover is moved from an open position toward a closed position.

5. The self-ligating bracket of claim 1 wherein said ligating archwire cover further includes a pair of side wing portions on either side of said locking tab, said pair of side wing portions each having a length that spans said archwire slot to thereby slideably engage a ledge on said second upper tie wing portion when said archwire cover is moved to a closed position.

* * * * *